United States Patent [19]

Ehrnford

[11] Patent Number: 4,521,191

[45] Date of Patent: Jun. 4, 1985

[54] CONDENSING INSTRUMENT FOR PACKING AND CONDENSING IN CONNECTION WITH PLACEMENT OF DENTAL COMPOSITE RESIN RESTORATIVE MATERIALS

[75] Inventor: Lars E. M. Ehrnford, Malmö, Sweden

[73] Assignee: Austenal International, Inc., Chicago, Ill.

[21] Appl. No.: 567,557

[22] Filed: Jan. 3, 1984

[51] Int. Cl.³ .............................................. A61C 3/08
[52] U.S. Cl. .................................................... 433/164
[58] Field of Search ................ 433/150, 153, 164, 89, 433/90

[56] References Cited

U.S. PATENT DOCUMENTS 2,903,794 9/1959 Carfagni ................................ 433/90

FOREIGN PATENT DOCUMENTS 0006757 1/1980 European Pat. Off. ............ 433/164

Primary Examiner—Robert Peshock
Attorney, Agent, or Firm—Wallenstein, Wagner, Hattis, Strampel & Aubel, Ltd.

[57] ABSTRACT

Condensing instruments are used for packing and condensing in connection with placement of dental composite resin restorative materials. These instruments are manufactured in metal or plastic material. Some composite resins however, contain hard particles and require a relatively large condensing pressure which causes abrasion of superficial fragments of prior art metal instruments. These fragments are confined in the restorative material and causes discoloration, often after oxidation. Plastic instruments quickly loose their surface finish, which may render it impossible to perform an adequate condensation. In order to provide an instrument which does not cause discoloration and which guarantees a durable function, at least one functional member (4 and/or 5) of the instrument consists of a metal alloy having a coating (6 and/or 7) of ceramic material which provides the working surface (8 and/or 9) of the functional member.

20 Claims, 5 Drawing Figures

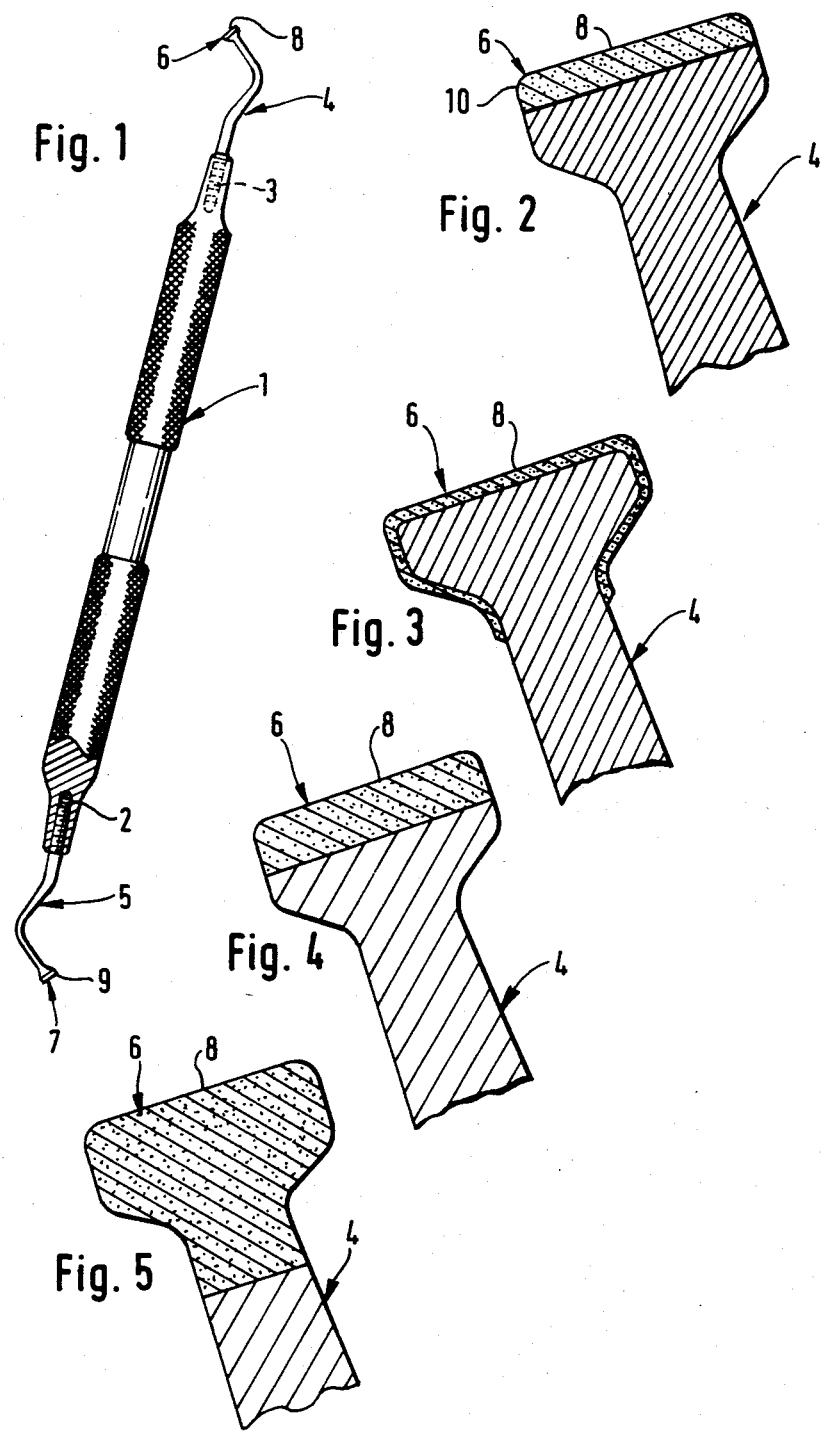

CONDENSING INSTRUMENT FOR PACKING AND CONDENSING IN CONNECTION WITH PLACEMENT OF DENTAL COMPOSITE RESIN RESTORATIVE MATERIALS

The present invention relates to a condensing instrument for packing and condensing in connection with placement of dental composite resin restorative materials.

To-day's composite resin materials have a potty or paste like consistency and thus, require no essential packing and condensing pressure. This means that the packing and condensing instrument may be manufactured in metal or plastic material without great demands upon surface hardness.

Composite resins under development, such as those defined in the U.S. Pat. No. 4,381,918, contain hard particles and require a relatively large condensing pressure which causes abrasion of superficial fragments of prior art metal instruments. These fragments are confined in the restorative material and causes discolouration, often after oxidation.

The use of plastic instruments also gives rise to certain problems, since such instruments quickly loose their surface finish. The rough surface thereby appearing is unfavourable as the composite resin thereby sticks to the surface to an extent which may render it impossible to perform an adequate condensation. The plastic instruments are inferior to metal instruments with regard to the resistance to heat treatment in connection with normal sterilizing procedures.

The object of the present invention is to eliminate these drawbacks and provide an instrument which does not cause discolouration and which guarantees a durable function. This is arrived at according to the invention substantially while at least one functional member of the instrument consists of a metal alloy having a coating of ceramic material which provides the working surface of the functional member.

The provision of a coating of ceramic material on the functional member consisting of a metal alloy eliminates the risk of discolouration and the pre-requisites for a durable function of the instrument are provided. Thereby, the instrument also acquires a high resistance to chemical and thermal action in connection with normal sterilizing or desinfecting procedures.

The invention will be further described below with reference to the accompanying drawings, in which FIG. 1 is a side view of the condensing instrument according to the invention;

FIG. 2 is a section through the end portion of the functional member of the instrument;

FIG. 3 illustrates an alternative embodiment of the functional member of the instrument;

FIG. 4 illustrates a section of a part of the functional member with a ceramic insert; and FIG. 5 illustrates a section of a part of the functional member with a ceramic insert of an alternative design.

The condensing instrument shown in FIG. 1 is intended for packing and condensing in connection with placement of such dental composite resin restorative materials that require a relatively large condensing pressure. The condensing instrument comprises a handle member 1 of metal or plastic. The handle member 1 has two threaded bores 2 and 3 into which functional members 4 and 5 are tightened. Alternatively, the condensing instrument may consist of a unit, wherein one or more functional members 4 and/or 5 are integrated.

In order to eliminate the risk of discolouration and provide the pre-requisites for a durable function of the instrument, said functional members 4 and 5 are made of a metal alloy and provided with coatings 6 and 7 of ceramic material defining the working surfaces 8 and 9 of said members 4 and 5.

One example of manufacturing a condensing instrument according to FIG. 1 is that on an amalgam condensing instrument, the end surfaces of the functional members 4 and 5 of stainless steel are ground clean with a coarse stone, e.g. a carborundum stone. A porcelain paste of low fusing procelain or glass, e.g. Steeles Super Stain or Micro-Bond Natural Ceramic (Howmedica Inc.) is placed on the ground surface and thereafter, the instrument is placed in a furnace at the temperature required for sintering for about 15 minutes. Hereby, the porcelain paste is baked on the functional members 4 and 5. If the porcelain surface after baking is not sufficiently even, said surface may be ground planar and if needed, another heat treatment is performed to provide glossy working surfaces 8 and 9.

It is especially advantageous if the instrument is heated to the sintering temperature and thereafter cooled before the porcelain is applied. Hereby, an advantageous oxidation of the instrument is provided, whereby the porcelain obtains good adhesion of the metal surface and its oxide layer.

In order to eliminate or at least reduce the risk of fall off of the ceramic coating 6, 7, e.g. in connection with heat treatment of the instrument for sterilizing or desinfecting procedures, the functional members 4, 5 preferably consist of a metal alloy having a thermal expansion coefficient substantially corresponding with that of the ceramic coating 6, 7.

The ceramic coating 6, 7 may be of different types, preferably glass or porcelain, whereby low fusing porcelain of glaze type is most suitable. A preferred type of ceramic coating 6, 7 can be described as a low fusing feldspathic porcelain with a nominal composition as follows: $68.64 SiO_2$, $13.76 Al_2O_3$, $0.36 CaO$, $13.46 K_2O$, $2.29 Na_2O$ and $1.49 Li_2O$. However, ceramic coatings 6, 7 can vary considerably in their composition and can be applied by flame spray methods, plasma spray methods and/or conventional sintering methods as previously described.

The functional members 4, 5 of the instrument may consist of different types of metal alloys, preferably stainless steel, nickel chromium based alloys and/or cobolt chromium or titanium based alloys are used. Especially suitable in this case is the alloy VITALLIUM ®, since the use thereof provides good possibilities for a rigid and strong construction of the instrument. Furthermore, VITALLIUM ® permits good adhesion of the porcelain paste intended for this matter, preferably Micro-Bond Natural Ceramic (Howmedica Inc.).

The working surfaces 8, 9 of the ceramic material 6, 7 are preferably planar or somewhat convex. Hereby, the composite resin sticks or adheres less to the instrument. Reduced adhesion or tendency to sticking is also achieved if the working surfaces 8, 9 are finished and/or baked to a high polish.

To facilitate the control of whether the ceramic coatings 6, 7 have fallen off from the functional members 4, 5 or not, said coatings 6, 7 are preferably opaque.

The risk of loosening of the ceramic coatings 6, 7 may be reduced while the thickness of the coatings is about one millimeter or less and the risk of loosening of the edge portions of the coatings may be reduced by chamfering the outer edges 10 limiting the working surfaces 8, 9.

The ceramic coatings 6, 7 may be applied onto the functional members 4, 5 as is shown in FIG. 2 or e.g. as is shown in FIG. 3. In the latter embodiment, the ceramic coatings 6, 7 extend in behind the expanded end portions of the functional members 4, 5. There are other alternative embodiments of the instrument and the members forming part thereof. Thus, the instrument may comprise only one functional member 4 or 5, the functional member may consist of other metal alloys, e.g. alloys comprising nickel and chromium or titanium alloys, the ceramic coating may comprise other materials than glass or porcelain, e.g. zirconium oxide, quartz or aluminium oxide, preferably sintered to high density. The ceramic part 6, 7 can also be a type of ceramic insert, which could take the forms as illustrated in FIGS. 4 and 5. The ceramic insert can be attached to the functional member or handle member by use of adhesive cements and/or mechanical retention.

I claim:

1. A condensing instrument for packing and condensing in connection with placement of dental composite resin restorative materials, characterized in that at least one functional member (4 and/or 5) of the instrument consists of a metal alloy having a coating (6 and 7) of ceramic material which provides the working surface (8 and 9) of the functional member.

2. The condensing instrument according to claim 1, characterized in that the thermal expansion coefficient for the metal alloy of the functional member (4, 5) substantially corresponds with that of the ceramic coating (6, 7).

3. The condensing instrument according to claim 1, characterized in that the ceramic coating (6, 7) consists of glass or porcelain.

4. The condensing instrument according to claim 3, characterized in that the ceramic coating (6, 7) consists of low fusing porcelain.

5. The condensing instrument according to claim 3, characterized in that the ceramic coating (6, 7) consists of porcelain of a low fusing feldspathic type.

6. The condensing instrument according to claim 1, characterized in that the ceramic coating (6, 7) is applied onto the functional member (4, 5) by baking.

7. The condensing instrument according to claim 4, characterized in that the ceramic coating (6, 7) is applied onto the functional member (4, 5) by baking in connection with or after oxidation of the metal alloy of the functional member.

8. The condensing instrument according to claim 1, characterized in that the ceramic coating (6, 7) is applied onto the functional member (4, 5) by flame spray methods, plasma spray methods and/or conventional sintering methods.

9. The condensing instrument according to claim 1, characterized in that the functional member (4, 5) consists of an alloy comprising cobolt and chromium.

10. The condensing instrument according to claim 9, characterized in that the alloy of cobolt and chromium is Vitallium ®.

11. The condensing instrument according to claim 1, characterized in that the ceramic coating (6, 7) provides a planar or somewhat convex working surface (8, 9).

12. The condensing instrument according to claim 1, characterized in that the functional member (4, 5) has an expanded end portion and that the ceramic coating (6, 7) extends in behind the expanded end portion.

13. The condensing instrument according claim 1, characterized in that the ceramic coating (6, 7) defines a working surface (8, 9) which is finished and/or baked to a high polish.

14. The condensing instrument according to claim 1, characterized in that the ceramic coating (6, 7) consists of opaque material.

15. The condensing instrument according to claim 1, characterized in that the functional member (4, 5) consists of an alloy substantially comprising stainless steel or nickel and chromium or titanium.

16. The condensing instrument according to claim 1, characterized in that the ceramic coating (6, 7) is applied onto the functional member (4, 5) by means of an adhesive.

17. The condensing instrument according to claim 1, which utilizes as its working surface (8, 9) a preformed ceramic insert.

18. The condensing instrument according to claim 17, wherein the ceramic insert is fabricated from a material comprising $Al_2O_3$, quartz or similar material.

19. The condensing instrument according to claim 17, wherein the ceramic insert is attached to the functional member (4, 5) or handle member (1) by use of adhesive cements and/or mechanical retention.

20. The condensing instrument according to claim 17, characterized in that the functional member (4, 5) or parts thereof constitutes the ceramic insert.

* * * * *